(12) United States Patent
Neev

(10) Patent No.: US 8,535,298 B1
(45) Date of Patent: Sep. 17, 2013

(54) DEVICE AND A METHOD FOR TREATING VULNERABLE PLAQUE AND CARDIOVASCULAR DISEASES

(76) Inventor: Joseph Neev, Laguna Beach, CA (US)

(*) Notice: Subject to any disclaimer, the term of this patent is extended or adjusted under 35 U.S.C. 154(b) by 459 days.

(21) Appl. No.: 12/777,205

(22) Filed: May 10, 2010

Related U.S. Application Data

(60) Provisional application No. 61/176,785, filed on May 8, 2009, provisional application No. 61/252,471, filed on Oct. 16, 2009, provisional application No. 61/303,271, filed on Feb. 10, 2010, provisional application No. 61/308,990, filed on Feb. 28, 2010.

(51) Int. Cl.
*A61B 18/18* (2006.01)

(52) U.S. Cl.
USPC .................................. 606/7; 606/11; 606/17

(58) Field of Classification Search
USPC ............................................................. 606/7
See application file for complete search history.

(56) References Cited

U.S. PATENT DOCUMENTS

| | | | |
|---|---|---|---|
| 4,686,979 A * | 8/1987 | Gruen et al. | 606/3 |
| 4,785,806 A * | 11/1988 | Deckelbaum | 606/7 |
| 5,005,180 A * | 4/1991 | Edelman et al. | 372/57 |
| 5,720,894 A * | 2/1998 | Neev et al. | 216/65 |
| 6,547,780 B1 * | 4/2003 | Sinofsky | 606/10 |

\* cited by examiner

*Primary Examiner* — Armando Rodriguez
(74) *Attorney, Agent, or Firm* — J. Peter Paredes; Rosenbaum IP

(57) ABSTRACT

A device and a method for treating Vulnerable Plaque by pulsed focused energy is described. The present invention describe a device and a method for a) breaking through plaque blocking arteries (totally occluded arteries) so that wires and stents can introduced to open the blocked or totally occluded arteries, and b) applying a controlled amount of energy to VP (possibly with cooling or energy removal applied to the surface layers) so that at least some of the constituents of the VP are stabilized or denatured so they can no longer cause blood clotting or are stabilized to prevent emergence into the blood stream and thus prevent clotting. Additionally an imaging method (for example, OCT, side looking OCT, IVUS, Ultrasound, OCT, thermography, IR imaging, Florence imaging, luminescent imaging, MRI, Videography, or other imaging technologies, allow viewing of the progress of the damage caused to the VP blood clot—causing components or the progress in the stabilization of the VP. Imaging of the said treatment effect on the VP in time and space can thus be made simultaneously with the present invention proposed treatment and provide real time feedback on the progress and effect of the treatment described by the present invention.

21 Claims, 9 Drawing Sheets

FIGURE 5 and FIGURE 6
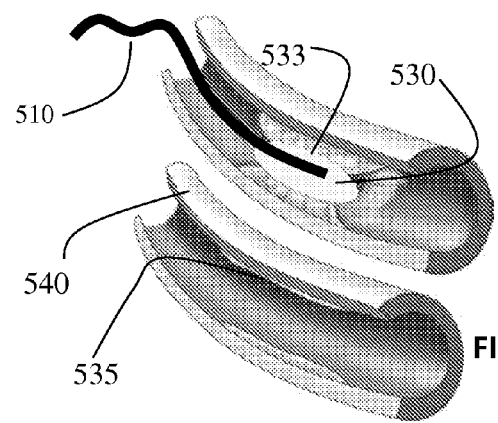
FIGURE 5B
FIGURE 5C
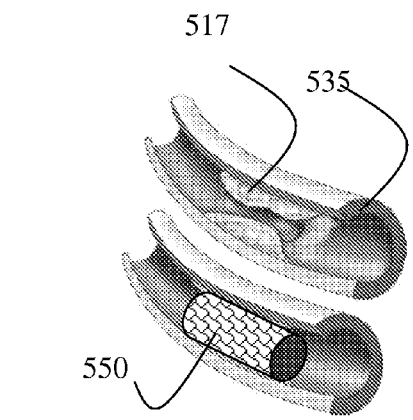
FIGURE 5A
FIGURE 5D
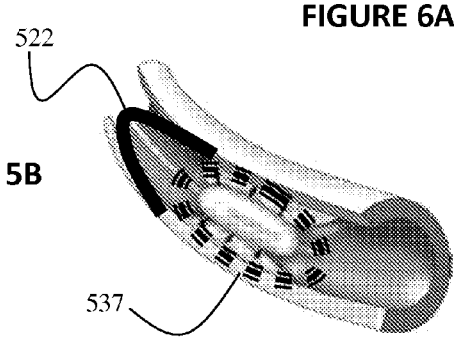
FIGURE 6A
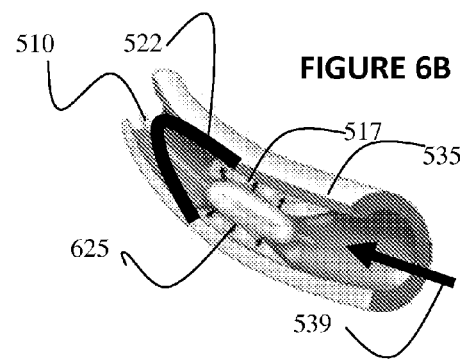
FIGURE 6B

DEVICE AND A METHOD FOR TREATING VULNERABLE PLAQUE AND CARDIOVASCULAR DISEASES

RELATED APPLICATIONS

This application claims priority to U.S. Provisional Application Ser. No. 61/176,785 filed May 8, 2009 entitled A Device And A Method For Treating Vulnerable Plaque In Arteries; U.S. Provisional Application Ser. No. 61/252,471 filed Oct. 16, 2009 entitled A Method And A Device For Substance Delivery Into Tissue And Skin And Tissue Alterations; U.S. Provisional Application Ser. No. 61/303,271 filed Feb. 10, 2010 entitled A Method And Apparatus For Tissue And Material Processing With Tailored Electromagnetic Pulses; and U.S. Provisional Application Ser. No. 61/308,990 filed Feb. 28, 2010 entitled A Method And Apparatus For Material And Tissue Processing And Therapy With Electromagnetic Energy, all of which are hereby incorporated herein by reference in their entireties.

BACKGROUND OF THE INVENTION

Cardiovascular diseases (CVD) are the most significant killer in the United states. Since 1900 CVD has been the No. 1 killer in the United States (See FIG. 8) every year but 1918. Nearly 2,500 Americans die of CVD each day, an average of one death every 35 seconds. CVD claims more lives each year than the next four leading causes of death combined, which are cancer, chronic lower respiratory diseases, accidents, and diabetes mellitus. In comparison, other causes of death in 2003 are: cancer, 554,643; accidents, 105,695; Alzheimer's disease, 63,343; HIV (AIDS), 13,544. The 2003 preliminary CVD death rates were 364.2 for males and 262.5 for females. Cancer death rates were 232.3 for males and 160.2 for females. Breast cancer claimed the lives of 41,566 females in 2003; lung cancer claimed 67,894. The death rates for women were 25.2 for breast cancer and 41.1 for lung cancer. One in 30 female deaths are from breast cancer, while one in 2.6 are from CVD. Based on preliminary 2003 mortality, CVD caused about a death a minute among females—over 480,000 female lives every year. That's more female lives than were claimed by the next five leading causes of death combined (cancer, COPD, Alzheimer's, diabetes and accidents). Over 152,000 Americans killed by CVD each year are under age 65. In 2002, 32 percent of deaths from CVD occurred prematurely (i.e., before age 75, close to the average life expectancy).

According to a 2006 Update, The American Heart Association estimated direct and indirect cost of cardiovascular diseases (CVD) for 2006 is $403.1 billion. In 2003, an estimated 6,821,000 inpatient cardiovascular operations and procedures were performed in the United States; 3.9 million were performed on males and 2.9 million were performed on females. Preliminary mortality data show that CVD as the underlying cause of death accounted for 37.3 percent of all deaths, or one of every 2.7, in the United States in 2003. CVD as an underlying contributing cause of death (1,408,000 deaths) accounted for about 58 percent of deaths in 2002.

The overall preliminary death rate from CVD in 2003 was 308.8. The rates were 359.1 for white males and 479.6 for black males; 256.2 for white females and 354.8 for black females. From 1993-2003, death rates from CVD (ICD/10 I00-I99) declined 22.1 percent. In the same 10-year period actual CVD deaths declined 4.6 percent.

Based on revised 2000 population data, the average life expectancy of people born in the United States in 2003 is 77.6 years. (CDC/NCHS) According to the CDC/NCHS, if all forms of major CVD were eliminated, life expectancy would rise by almost seven years. If all forms of cancer were eliminated, the gain would be three years. FIG. 8 illustrates the urgent need for a cure of CVD since CVD is by far the biggest killer of adults in the USA.

There is, therefore, a clear and urgent need for the solutions presented in this invention for treatment and prevention of CVD.

BRIEF DESCRIPTION OF THE DRAWINGS

FIG. 5 shows a simplified diagram of a device and method for treatment of VP.

FIG. 6 shows a simplified diagram of Optothermal and cooling treatment of VP.

DESCRIPTION OF PREFERRED EMBODIMENTS

Figure 1:
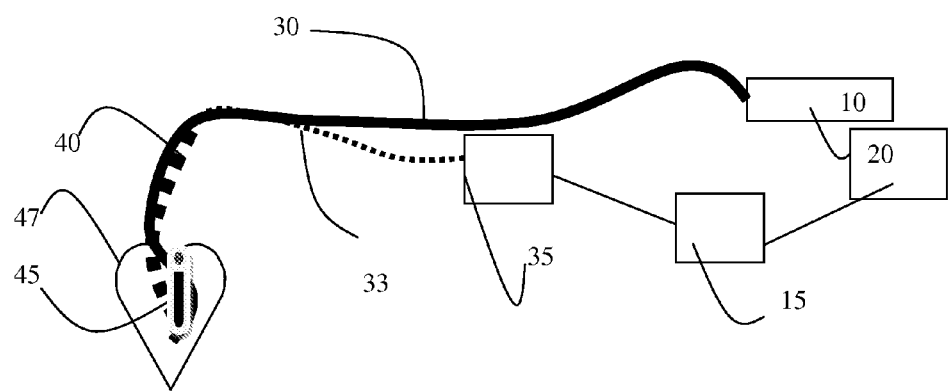
FIG. 1 is illustrates a simplified diagram of a device for treatment of VP.

One preferred embodiment according to the present invention includes a device comprising an energy source; a pressurized air (or other fluid or liquid) source; a synchronizing means; a trigger means and a means to direct each of the previous elements to a target covered by fluid.

Another preferred embodiment according to the present invention comprises firing a pressurized fluid (for example air, gas, cryogen or liquid); directing the pressurized fluid to a fluid-covered target; synchronizing the emission of the firing of the pressurized fluid with an energy source; and firing the energy source a short time later while the target is still removed (i.e., before the fluid returns to cover the target area). Another preferred embodiment according to the present invention comprises a therapy that can cooperate or replace wire-led stent therapies to delivery therapeutics treatment though optical fibers and Hollow Wave Guides (HWG). Optical fibers and HWG can be made as small as 50 micrometer in diameter or possible even smaller.

In another preferred embodiment according to the present invention, a method for treating CVD is described utilizing energy carrying optical fibers or HWG. Among other things, this technology can fulfill multiple functions. For example:
1. Deliver energy for removing plaque and opening totally occluded plaque plagues in the arteries.
2. Deliver energy for disabling vulnerable plaques
3. Fire energy in all directions (forward and 360 degrees)
4. In combination with SEE achieve 3D imaging of some of the smallest vessels with a single fiber
5. In combination with various OCT techniques image tissue three dimensionally for mapping tissue structure and morphology 6. In combination with luminescence emission and fluorescence emission, image and analyze tissue composition and chemical makeup.
7. In combination with nanoparticles, HAS, PDT, and TiO2, allow selective destruction of targeted regions in the arteries.

Devices

One embodiment according to the present invention includes a device for treating CVD comprises a minimally invasive electro-optic and laser surgical procedure for detection, imaging and treatment of vulnerable plaque. This embodiment includes the use of femtosecond lasers for subsurface interaction with subsurface components of the plaque to eliminate the risk of clot-forming leakage. The technology combines imaging diagnostics capabilities with electromagnetic energy-based microsurgery for the removal or reduction of fatty and calcified plaque protrusion that slow or block arterial blood flow. As an adjunct to stent technology, (which CFT hopes will ultimately be replaced by intravenous probe surgery) the technology can assist in allowing insertion of wires and stent where total occlusion occurs, and allow clearing and refurbishing of existing stents that are partially or fully occluded.

DETAILED DESCRIPTION OF THE EMBODIMENTS

Some aspects of the invention relate to treating arterial plaque blockage with energy by either removing at least some of the plaque using a controlled delivery of energy or by using controlled delivery of energy to targeted layers of plaque or lipids in the arteries. In this respect especially dangerous and clot-creating plaque and components of the arteries can be disabled or destroyed while sparing other components of the arteries needed for proper functioning and proper blood flow. An Embodiment of the Invention is Shown in FIG. 1.

FIG. 1 shows an energy source 10. An example energy source 10 includes a Femto second laser or other short pulse laser, a CW laser with sufficient control to turn the beam on and off for a duration that will allow denaturation of the targeted tissue or other pulsed or time-duration-controlled energy source for example pulse ultrasound energy source, pulsed RF energy source, pulsed electrical energy source, pulsed microwave energy source, pulsed x-ray energy source, pulsed uv-energy source, pulse radio wave energy source, pulse heater, pulsed magnetic energy source, pulsed electric energy source, pulsed chemical energy source, pulsed phonon energy source, pulse shock wave energy source, pulsed acoustic wave energy source, pulsed ion energy source, pulsed proton energy source, pulse nuclear energy source, or other pulsed energy sources known to man.

In one example, the energy source 10 is a pulsed laser that can be controlled by a controller 20. The energy from the laser source is conducted through a conduit 30, such as an optical fiber or a hollow wave guide, toward the target material.

Preferably, the energy conduit 30 is located within a catheter 40, which directs the energy towards the targeted material 45 (e.g., a heart 47 with arteries 45). A secondary imaging and diagnostic system 35 may also be used, such as a Laser induced plasma spectroscopy system (LIPS), (e.g., a LIPS from Ocean Optics Corporation, Dundee Fla.). LIPS systems often include their own energy source, such as an Nd:YAG with a few ns pulse 100 mJ pulse energy source lasing at the fundamental wavelength of 1064 nm or one of its harmonics (SH at 532 nm, Third Harmonic, or fourth harmonic at 266 nm). Alternatively, a custom energy source 10 as the source of pulse energy for the LIPS system may be used.

The LIPS source is also coupled to the target area 47 and 45, via a catheter or conduit 33 such as an optical fiber or a hollow waveguide.

The catheter or conduit 33 may include several components such as IVUS imaging, OCT imaging, US imaging, forward looking OCT or forward looking IVUS imaging or other imaging systems known in the art. A computer/processor 15 controls the input and output to and from the various components of the system.

Figure 2A:
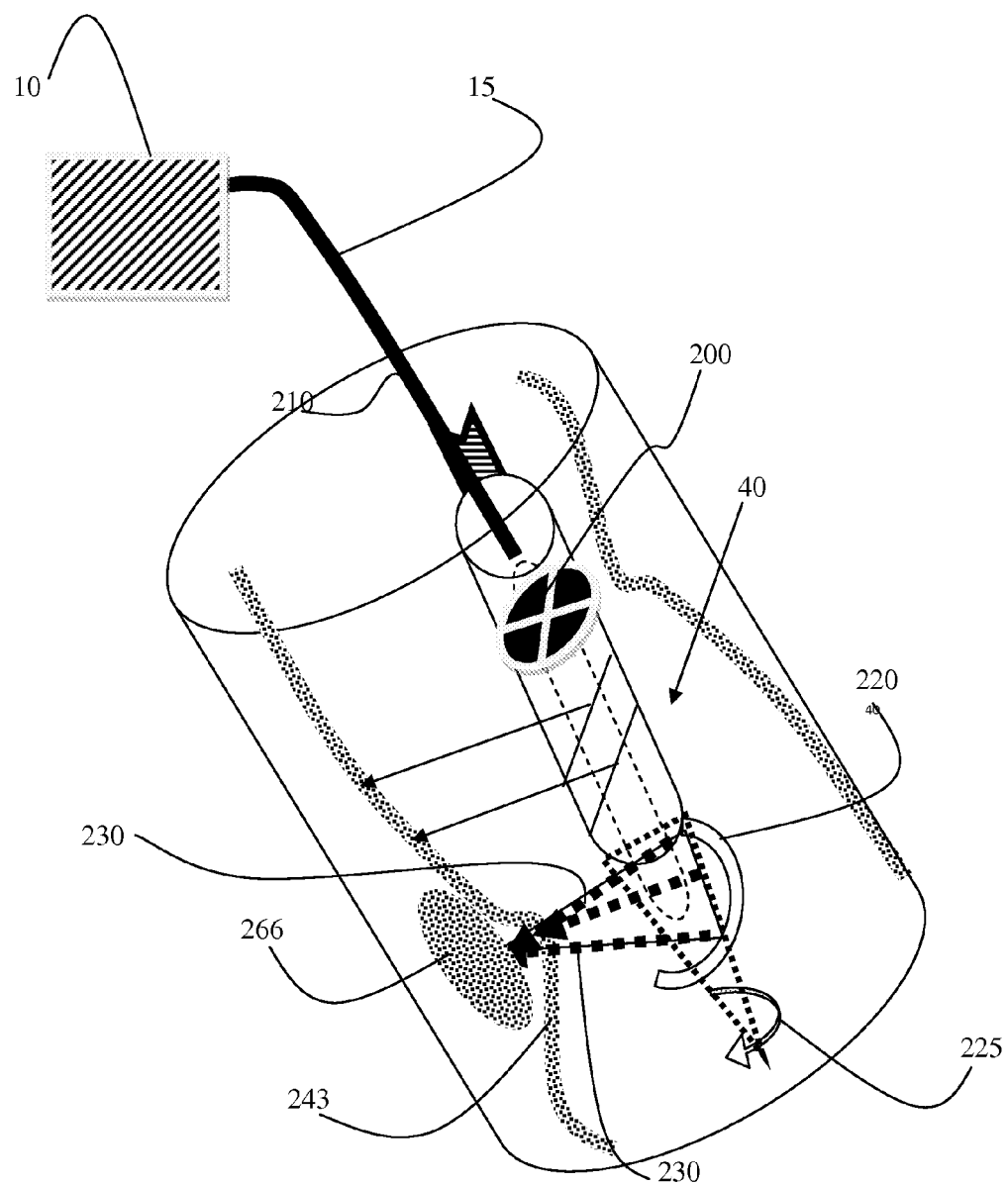
FIG. 2A shows another simplified diagram of a device for treatment of VP under the surface of the endothelium.

An energy-coupling catheter 40 is shown in greater detail in FIG. 2A. A propeller 200 may be used with a liquid or fluid flow 210 to move the propeller or rotator 200 and allow rotation of a mirror 220 or other focusing, reflector/delivery element 220. The rotation is shown by the arrow 225. The reflector, or mirror element 220 may be a convex mirror 220 thus allowing the delivery beams 230 delivered through the conduits 30 and 37 to be focused.

The focused energy beam is delivered to the targeted material 240 such as a plaque or vulnerable plaque 240. This energy beam 230 from the energy source 10 may optionally be affected through three dimensional focusing of the beam 230 under the surface of the targeted material 243, so that the surface of the plaque or targeted material or vulnerable plaque 240 is NOT ruptured, but the plague underneath the surface is damaged, shrunk, denatured, destroyed or otherwise rendered less dangerous. This treatment may optionally be enhanced by depositing or accumulating an absorbing material, absorption enhancing material, nano particle, PDT compound or other substance 266 capable of enhancing the interaction between the incoming beam 230 and the targeted region or plague 240. Optionally such nano particles 266 or other interaction enhancing substance 266 may allow interaction under the surface of the plaque or vulnerable plaque 243 without damaging said surface of the plaque 243, thus not allowing dangerous debris or macrophages to escape into the blood stream as described in more detail later in this specification.

The fluid from the fluid flow 210 that moves the propeller 200 may also allow removal of blood or other debris from the vicinity of the targeted region and may optionally allow better coupling of the beam to the targeted material, better index matching, and optionally better cooling of the surface of the vulnerable plaque so it is substantially less damaged by the incoming beam 230.

Figure 2B:
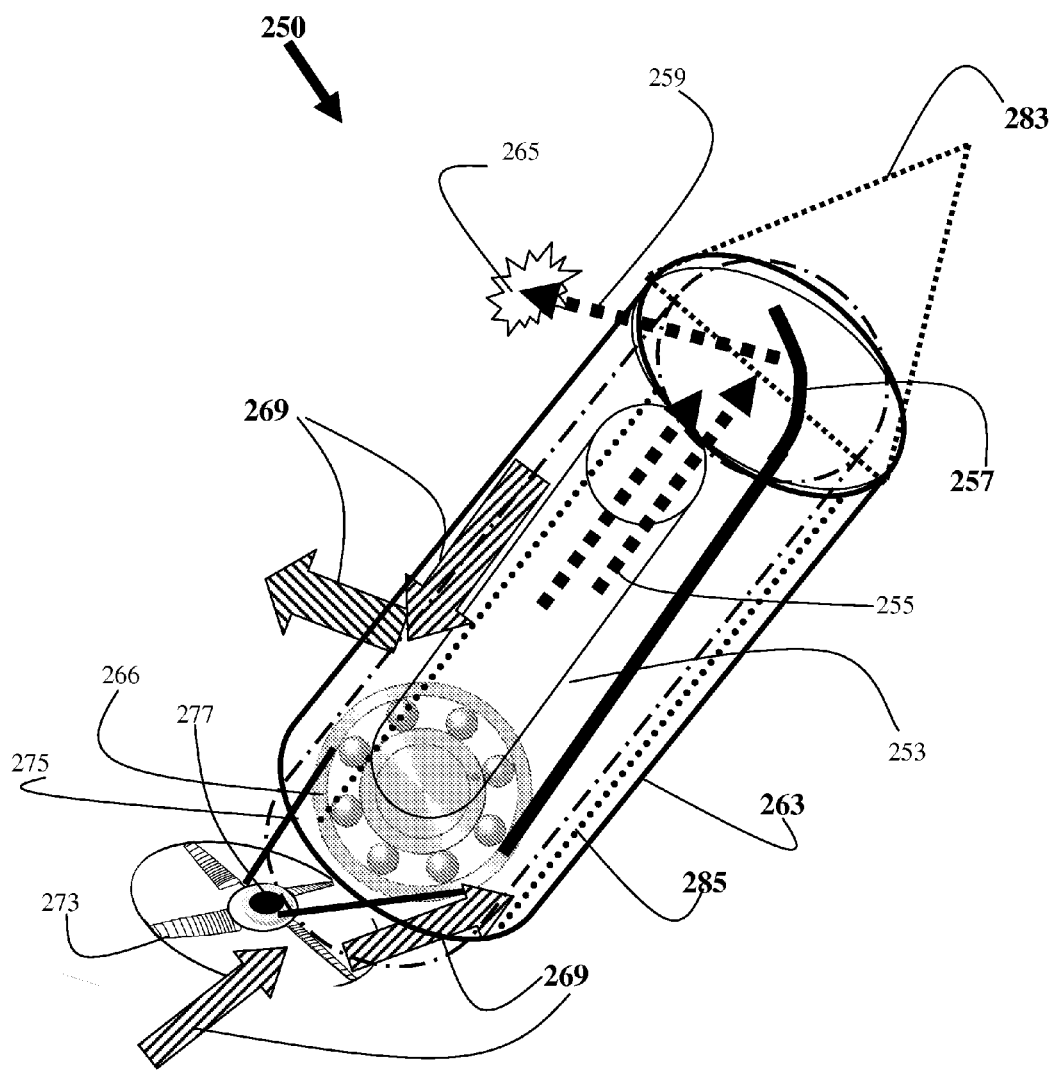
FIG. 2B shows another simplified diagram of a device for treatment of VP under the surface of the endothelium.

As an example, a more specific exemplary design and operation of the treatment head 250 is shown in FIG. 2b.

The Hollow Wave Guide (HWG) 253 delivers the energy pulses 255 to a focusing/redirecting element 257, for example, a concave mirror 257. The redirected energy pulses 259 pass through the expandable member (for example, a balloon that can be expanded with saline water pressure, containing an exemplary circulating saline liquid) 263 that are substantially transparent to the pulses energy, and interact with the targeted volume 265.

The focusing element, for example a concave mirror 257, can, for example, be connected to a rotating member, for example a ball bearing member 266, so that it can be rotated to redirect the beam to any desired direction. The rotation of the ball bearing 266 and the connected concave mirror 257, can be propelled, for example, through the flow of a fluid or liquid, 269, for example, a saline solution 269, wherein saline solution 269 or other flowing liquid 269 is directed through blades of a rotor 273, for example rotor blades such as those known in the art, so that motion is created, said motion of the blades is then transferred, for example with the connecting structures 275 to the ball bearing 266. Exemplary breaks 277 in the rotor blades 273, or other propelling means 273 may be used by the operator or in an automated, or computer-controlled design, to willfully control (stop or allow to spin) the motion of the rotor 273 and thus the spinning of the focusing element 257. The flow of the fluid 269 helps keep the targeted tissue cool and also expand the walls of the containing structure (for example an expendable balloon) 263 to allow it to make contact with the targeted tissue. Additionally or optionally, a member 283 may be made of a harder material and a optionally a pointed design to allow it to more easily penetrate and guide the treatment head 250 through the artery and possible protruding structures in the arteries such as calcified or lipid plaque.

Additionally or optionally, harder members 285 can be embedded in the containing structure (e.g. an expendable balloon) 263 to provide it with strength and a frame to follow the guidance of the leading/penetrating top, 283.

In one embodiment, the energy source 10 emits energy at a variable repetition rate that can range from a single shot to as much as 200 MHz, or at least a few hundred KHz, for example 250 KHz or 100 KHz, or 10 KHz, or 1 KHz, or 500 Hz. A diagnostics system 35 (e.g., a laser induce plasma spectroscopy or LIPS), may be synchronized with the energy source 10 or may have its own energy source (e.g., a ns Nd:YAG laser) to monitor the emission from the target material to allow detection and monitoring of the characteristics of the target material and its surroundings.

For example, in this embodiment, the monitoring system may monitor plasma luminescence emission at a repetition rate such that the period between sampling is between about 1 ns and 10 second, or between about every 0.1 microsecond and about every 5 seconds, or between about every microsecond and about every 1 seconds, or between about every 10 microseconds and about 0.1 seconds, or between about every 100 microsecond and about every 10 milliseconds, or between about every microsecond and about every microseconds, or between about every 1 ms and about every 100 milliseconds. Alternatively or additionally, the diagnostic system 35 measure the characteristics of the targeted surface sufficiently often to allow the operator to substantially avoid damaging interaction with unwanted material other than the targeted material, for example the material targeted for modification or destruction. For example, if the energy source emits energy in pulses of pulse repetition rate of for example about 1 KHz, and remove or modify target tissue or target material at a rate of about 0.1 micrometer depth per pulse to about 5 micrometer per pulse, a sampling rate of about 1 KHz (i.e. about every 1 ms) to about every 10 milliseconds, will allow the operator to determine the targeted tissue properties about every 0.1 micrometer to about every 50 micrometer, so that when the system detect a new or modified tissue, it can be stopped within about as low as 0.1 micrometer (or possibly even with greater resolution) to within about 50 micrometer at most. These resolutions allow very fine control of the amount of material removed, particularly if the monitoring system samples at the higher repetition rates of the ranges described above (e.g., to within as low as about 100 nm or less).

In another embodiment, the targeted tissue is injected with a substance 267 capable of absorbing at least some of the radiation generated by the energy source 10. The absorbing substance can be carbon base absorber, a TiO2, nano particles, PDT based substance, or other substances capable of absorbing said source energy. The Energy is then delivered to the targeted plaque via a hollow wave guide, a fiber, or other substance. Alternatively or additionally, the energy can be delivered to the inside the plaque region with a needle-like delivery conduit.

Additionally or alternatively, the energy from the energy source 10 delivered through the beam 230, is delivered through a interface 269, such as a balloon with circulating coolant fluid or liquid inside it. A surface of the balloon is in contact with the surface of the targeted material or plaque so that the cooled balloon surface protects the surface of the of the plaque or target material and prevents rupture. Meanwhile, the energy from the beam 230 penetrates to within the target material or plaque to substantially denature or otherwise modify the targeted material or plaque so that it shrinks, is rendered incapable of causing blockage or heart attacks, incapable of rupturing or is incapable of negative effects in a mammal body or mammal heart.

Figure 3:
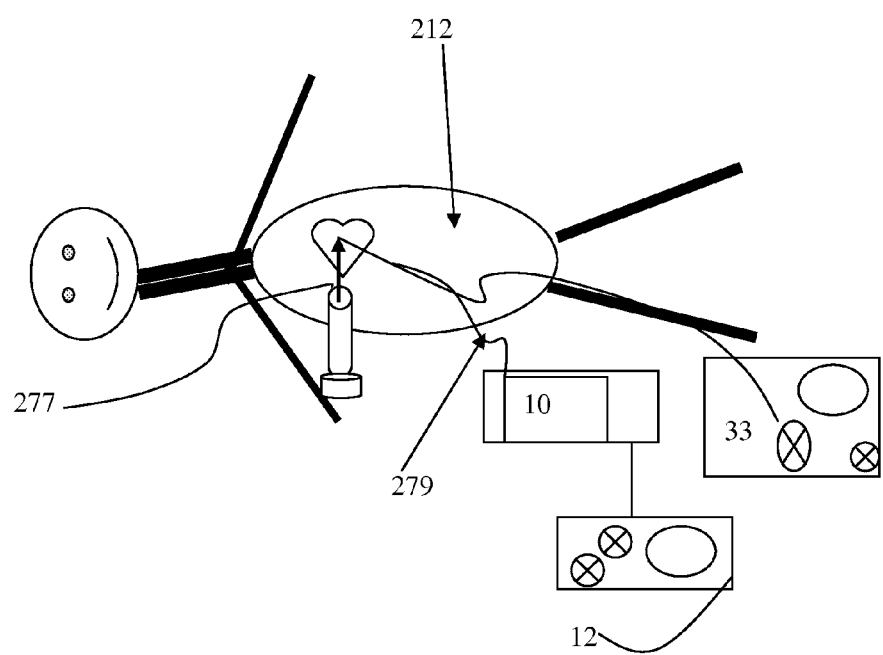
FIG. 3 shows how a device for treatment of VP may be used.

Another embodiment according to the present invention is shown in FIG. 3. Here, the energy from the energy source 10 is coupled to a conduit, such as an optical fiber, a hollow wave guide or other conduit 277. The energy is then delivered through an injector and a needle-like delivery member 279 directly into the region of the plaque formation. The energy source 10 is then activated through the use of a control box, and the modification or reduction in the presence of the plaque is accomplished through the action of the energy from the energy source 10 with or without the aid of an absorbing substance, for example, nanoparticle, gold nano particles, PDT agent, carbon based absorber, TiO2 or other substances capable of absorbing or otherwise being activated by the energy from the energy source 10. Optionally, an imaging system 37 and 33 is coupled to a catheter to allow inside-the arteries imaging of the targeted material or plaque. For example, an OCT, an IVUS, a forward looking ivus, an ultrasound imaging, a cat scan, an x ray system, an angioplasty system, an angiogram, a PET system, MRI system or other imaging system or method known can be used.

Embodiment

Figure 4:
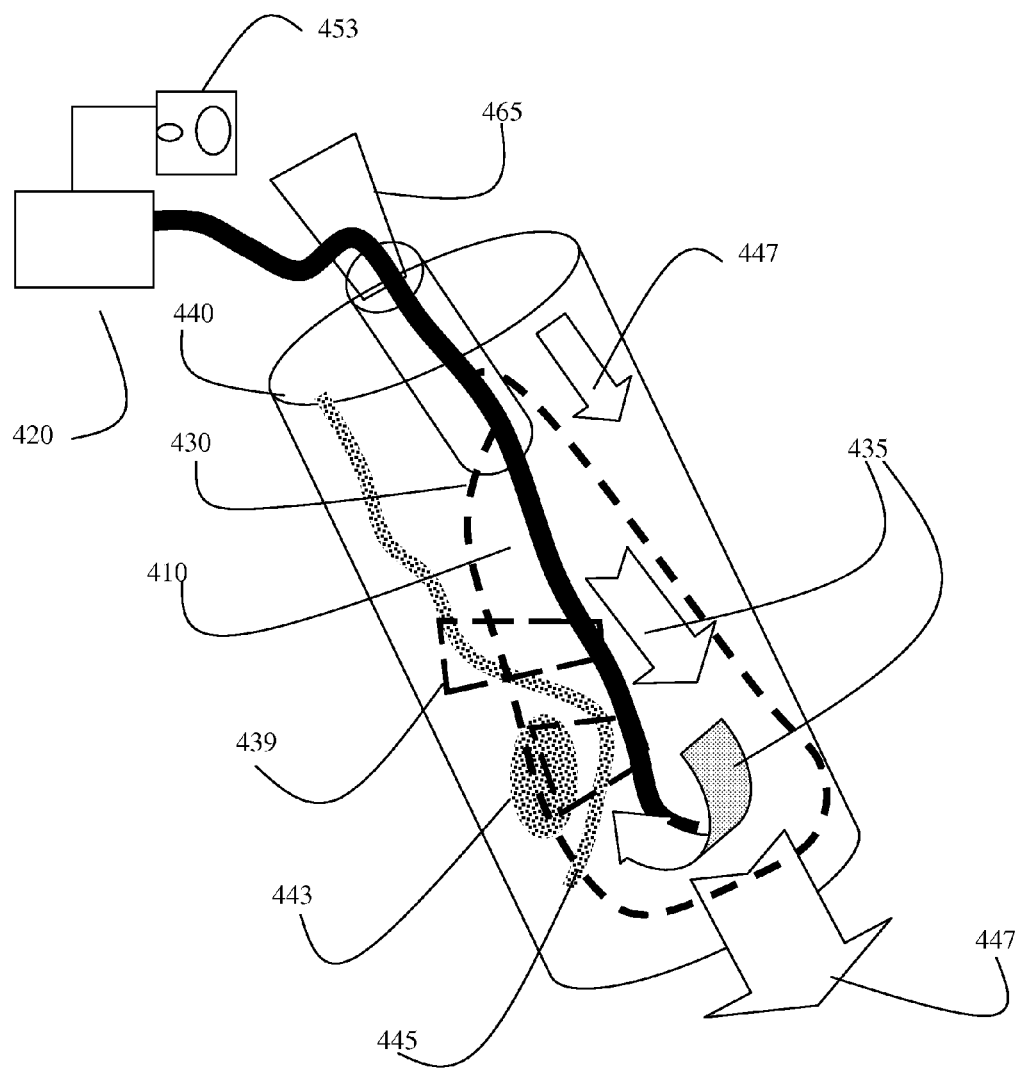
FIG. 4 shows a simplified diagram of a device for the treatment of VP compromises a surface cooling balloon.

Disablement of Plaque—FIG. 4

FIG. 4 illustrates another embodiment according to the present invention having a catheter head 410 that contains a side firing conduit energy source 420. It may also contain other imaging sensors. At least the energy source side firing member is contained within a balloon 430. The balloon is capable of containing circulating fluid 435 and is capable of expending and contacting the blood vessel walls 440 and also the protruding plaque elements 445 elements that occur in blood vessels. An imaging, detecting, sensing, or monitoring member 450 is used to detect plaque and image the interior part of the blood vessels or the target material.

An imaging member, or any other imaging or sensing member may be used for imaging, detection, or sensing 450 the target material, the inside of a blood vessel or the blood vessels plaque or tumors. For example, such imagining or sensing member of a technology that may be used for imaging, detection or sensing, may include: a LIPS element identifying head an OCT, a spectral domain OCT, a phase-sensitive OCT, a time domain OCT, an infrared imaging source, an ultrasound, a forward looking ultrasound, an optical imaging source, forward looking IVUS, an IVUS, an MRI, CAT Scan, an x-ray member source, A spectrally encoded imaging member (SEE), a magnifying imaging member, an endoscope, or any other imagining or sensing member of a technology that may be used for imaging, detection, or sensing 450.

When the imaging, detecting or sensing element 450 identify a plaque or a tumor or other target material for destruction, the energy source is activated and the side firing conduit head directs the energy towards the target material. Before, during or after the energy source is activated (or any combination of before during and after), the circulating fluid is activate to allow the fluid to cool the surface of the targeted material. Other cooling elements may also be used to cool the surface of the targeted material. The circulating fluid 435 is preferably transparent to the energy beam, allowing it to pass through the circulating fluid and into the target material or plaque or tumor.

In an alternate embodiment, the circulating fluid is preferably capable of cooling the surface of the target material and thereby substantially preventing damage or rupture of the surface of the target material. For example, the circulating fluid can be water, cooled water, cryogen, Freon, gas, cooled gas, gas with lower temperature then the surface ambient temperature, fluid, cooled fluid, mixture, cooled mixture, or any other substance capable of circulating within the balloon. This fluid can also, cool the surface of the target material before during or after the delivery of the energy from the energy source to the target material. Additionally, this fluid is preferably substantially transparent to the beam of energy so that the energy can substantially be delivered to the target material or tumor or plaque.

The energy source 420 may deliver one of the following example energies: light energy, laser energy, Electromagnetic energy, an RF energy, an electrical energy, an Ultrasound energy, a microwave energy, magnetic energy, chemical energy, mechanical energy, acoustic energy, x ray energy, gamma rays energy, proton energy thermal energy acoustic energy or any other form of energy.

In one embodiment the energy from the energy source 420 can pass through the surface of the target material substantially with less absorption then it absorbed in the body of the target material volume. In another embodiment the energy substantially penetrates through most of the targeted material.

Using known properties (optical thermal, mechanical, chemical and others) of the target material, the operator can calculate what are characteristics of the energy beam and cooling substance design to minimize the non beneficial effects of the target material.

For example, if the operator would like to reduce the chances of vulnerable plaque leaking clotting agents into the blood stream, the operator can use known properties of the plaque to activate a laser beam (e.g., a KTP beam at 532 nm) to transverse the balloon surface and the plaque surface to coagulate at least part of the plaque and reduce its size and negative impact potential.

In a more specific example, a CW 532 nm 10 W radiation can be used to deliver a CW beam of energy into a 1 cm thick plaque by activating the beam for about 5 or 10 seconds with the presents of cooled water circulating in a transparent medical grade plastic balloon before during and after the activation of the energy. Optionally, an endoscopic camera and optionally a thermal (or IR) camera may monitor the surface of the plaque to assure the operator that no excessive damage (e.g., charring or rupturing of the plaque surface) occurs. Temperature sensing, IVUS, OCT imaging, and visual color monitoring can indicate to the monitoring system and operator what is the end point of the application of the beam of energy, for example laser beam at 532 nm wavelength.

Alternatively or additionally, the energy source can emit RF, Ultrasound, pulsed light, pulsed electromagnetic radiation, pulsed electrical energy, pulsed magnetic energy, or pulsed microwave, or other forms of energy.

Alternatively or additionally, the energy source can be a light, laser, ultrasound, or other energy source that can be focused underneath the surface of the target material to cause selective damage below the surface of the target material or plaque.

Alternatively or additionally the catheter head also has the ability to apply pressure to the surface of the target material tumor or plaque and optionally cause at least some deformation to the surface of the target material plaque or tumor.

FIG. 5 are examples illustrating how the invention may be used to treat blockage and VP plaques in an artery. FIG. 5A shows a plaque that can block at least some of the blood flow by restricting the size of the opening in the artery. The plaque and VP 517 deposited on the inner surface of the wall of the artery 535 is building outward towards the cavity used for blood flow.

FIG. 5D shows a traditional stent 550 known in the art to be used to reduce the size of the plaque 517 blockage by expending the stent 550.

FIG. 5B shows a non-limiting exemplary device as contemplated by the present invention. For example, a fiber or a HWG 510 is inserted into the artery with its treatment head region 533 covered by an expandable balloon 530. After the balloon and treatment head are inserted to the plaque area, the balloon is expanded to allow treatment as described elsewhere, herein. FIG. 5C shows the cleared arterial wall 540 and the reduced/treated plaque and VP size, 535.

FIG. 6 Shows Another Embodiment of Treatment of Vulnerable Plaque

A HWG treatment tip 533 is inserted to the narrowing passage restricted by the plaque 517 and the balloon 530 is expanded 537 to provide pressure and contact with the plaque surface 517. (As mentioned elsewhere herein, the fluid circulating in balloon can provide cooling to the surface of the plaque 517). The energy source is activated and radiation (shown by the arrows 625) is directed towards the arteries walls 535 and the VP 517 to allow shrinkage of the protruding plaque and disablement of the VP 517. Additionally in another example, a sieve, strainer or filter 522 to catch and collect any debris, fragments, or lipids dislodged from the treated plaque, arterial walls 637 or VP 717. Such a filter, sieve or strainer, 522, may then be retrieved and withdraw with the device at the end of the treatment so that the dislodged debris or lipids fragments are removed from the body. An exemplary direction of blood flow is sown by the arrow 539.

One of the dangers associated with the treatment of vulnerable plaque (VP) is the release or leakage of macrophages into the blood stream—resulting in the formation of blood clots that can completely block the plaque-clogged blood vessels. One embodiment of the present invention contemplates disablement of the VP components by the application of thermal treatment. In one embodiment, the energy is delivered to the target area through the use of a conduit capable of conducting said energy. For example, if a light energy or electromagnetic energy (EM) is used, the energy can be delivered through the use of an optical fiber or a hollow wave guide. The energy is delivered through a balloon or other inflatable member that allow a cooling fluid to circulate through it.

In one embodiment the invention contemplates a method for treating cardiovascular diseases and reducing the probability of a heart attack with the following process. The method comprises of 1. Providing an energy source,
2. Delivering said energy from the energy source to the vicinity of the targeted VP using a energy conduit (for example, such conduit can be an optical fiber, or a hollow waveguide, or another conduit capable of delivering the energy to vicinity of the targeted material)

3. Activating the delivered energy so it at least partially denature at least some of the target material, for example VP, and the VP components that can lead to blood clotting.
4. Optionally or additionally, removing some of the targeted material, for example VP or other substance that cause constriction or limit the ability of blood vessels to transport blood.

In another embodiment the invention contemplates a method for treating cardiovascular diseases and reducing the probability of a heart attack with the following process. The method comprises of 1. Heating the targeted area (or otherwise treating it) so that the elements within the targeted area, for example, within the arterial plaque, are at least partially disabled so they are not able to cause blood clotting. For example, this can be done by exposing said targeted material, for example, VP, to thermal energy or optical energy, or electrical energy or EM energy, or chemical energy, or RF energy, or Ultrasound energy, or mechanical energy, or magnetic energy, or electromagnetic (EM) energy, or X-Rays, or other forms of energy that disable the target material ability to cause blood clotting.
2. Then ablate, vaporize or remove at least some of the targeted material, for example through ablation, laser ablation, electrical cutlery, electro surgery, ultrasound, mechanical energy, electrical or thermal energy, or other material removal or material ablation methods or devices known in the art.

Another embodiment of the present invention comprises (the steps of):

1. Providing an catheter capable of being inserted into the an artery,
2. Imagining abnormal or suspected target tissue, for example, an arterial wall location
3. Optionally activating a surface cooling member, for example a balloon filled with surface cooling fluid in contact with the arterial wall surface
4. Activating an energy source capable of thermally affecting the arterial wall components to disable blood clot-forming components of the tissue within said location, the energy from the energy source is delivered to the target location through an energy conduit brought to the target location by the catheter,
5. Keeping the energy flowing into the targeted tissue for a time duration sufficient to affect the arterial wall components so that blood clot-forming components of the tissue within said location are at least partially disabled,
6. Optionally rotating the catheter so that the energy is delivered to other suspected tissue locations as needed,
7. Optionally ablating or removing at least some of the targeted material or plaque along the arterial wall.
8. Optionally analyzing the arterial walls components for the type and condition of the material along the target material and arterial wall. Such analysis may include one or more of the following analysis methods:
   Luminescence spectroscopy,
   Fluorescence spectroscopy,
   IVUS
   Ultrasound
   OCT,
   LIBS
   LIPS
   Spectroscopy,
   Thermography,
   Emission Spectroscopy
   Temperature measurements,
   Angioplasty
   Chemical analysis
   Mechanical Analysis
   Stress analysis
   Analysis of elastic property
   Visual diagnostics
   Color diagnostics
   Multi-photon Spectroscopy,
   Microscopy
   Photo-imaging
   Interferometery
   Speckle interferometery
   Other imaging methods or analysis methods known in the art.
9. Removing or modifying additional material in response to the analysis described by step 8.
10. Continuing to move the catheter along the arteries or blood vessels until all suspected treatment site are treated.
11. Additionally or optionally removing material from the obstruction or protruding plaques or growth from the targeted material or arteries.
12. Optionally or additionally smoothing or reshaping the inner surface of the targeted material or treated arteries to enhance blood flow.
13. Additionally or optionally changing the properties of the targeted material or targeted arteries so to improve strength or improve blood flow. For example, such improvement in the qualities of the arteries material can consist of smoothing the inner linings of the arteries or smoothing the endothelium, or removing some or all the plaque or debris or lipids adhering to the inner surface of the arteries.
14. The present invention contemplates bringing energy into a the lumen and imaging the or otherwise monitoring and the lumen walls, for example, using a IVUS, OCT, imaging camera and fibers, or by using other method of viewing the walls as described elsewhere herein.
15. The energy, for example, laser energy can be delivered as shown in FIG. 5 using conduit 510, for example, an optical fiber 510 or hollow wave guide 510 and inserting the delivery conduit 510 to the vicinity of the VP 520. A balloon 530 or other energy mediating member, 530 is then inflated, and makes contact with the arteries walls 540. The energy source is activated and the energy from the fiber, for example using a side firing fiber, is delivered to the plaque as shown in 610 of FIG. VP 6B. An energy removing fluid 620 can be circulated in the balloon 530 and keep the surface of the plaque 535 or targeted lumen walls 540 undamaged and enraptured. The content of the VP 540, for example, macrophages, cytokines, monocytes, or other lipids and VP components can be substantially modified or substantially damaged by the source energy. Subsequently, a stent or another more permanent reinforcing structure 550, can be inserted as shown in FIG. VP5D. FIG. 6A shows the energy delivered through the conduit 510, for example, an optical fiber 510 or hollow wave guide 510 to the energy mediating member, for example, a balloon. The energy is then irradiated through the walls of the member or balloon, as shown by the arrows 625, and creates a heated zone 635 where the energy elevates the temperature of the plaque or targeted material, 535 to disable or denature the plaque components capable of enhancing or creating blood clotting. For example, the optical energy or elevated temperature profile under the plaque surface, can cause transformation of the VP components such as cytokines, lipoproteins, white blood (monocytes) and macrophages thus reducing the risk of heart attacks, blood clots and strokes.

The present invention contemplates bringing energy into a lumen and imaging or otherwise monitoring and the lumen walls, for example, using a IVUS, OCT, imaging camera and fibers, or by using other method of viewing the walls as described elsewhere herein.

The energy, (e.g., laser energy) can be delivered as shown in FIG. VP5 ? using conduit 510, for example, an optical fiber 510 or hollow wave guide 510 and inserting the delivery conduit 510 to the vicinity of the VP 520. A balloon 530 or other energy mediating member 530 is then inflated, and makes contact with the arteries walls 540. The energy source is activated and the energy from the fiber (for example using a side firing fiber) is delivered to the plaque as shown in 610 of FIG. VP 6B. An energy removing fluid 620 can be circulated in the balloon 530 to prevent the surface of the plaque 535 or targeted lumen walls 540 rupturing or becoming damaged. The content of the VP 540, for example, macrophages, cytokines, monocytes, or other lipids and VP components can be substantially modified or substantially damaged by the source energy. Subsequently, a stent or another more permanent reinforcing structure 550, can be inserted as shown in FIG. VP5D. FIG. 6A shows the energy delivered through the conduit 510, for example, an optical fiber 510 or hollow wave guide 510 to the energy mediating member, for example, a balloon. The energy is then irradiated through the walls of the member or balloon, as shown by the arrows 625, and creates a heated zone 635 where the energy elevates the temperature of the plaque or targeted material, 535 to disable or denature the plaque components capable of enhancing or creating blood clotting. For example, the optical energy or elevated temperature profile under the plaque surface, can cause transformation of the VP components such as cytokines, lipoproteins, white blood (monocytes) and macrophages thus reducing the risk of heart attacks, blood clots and strokes.

A Device for Treating CVD the Device Comprises: An Energy Source

Figure 9:
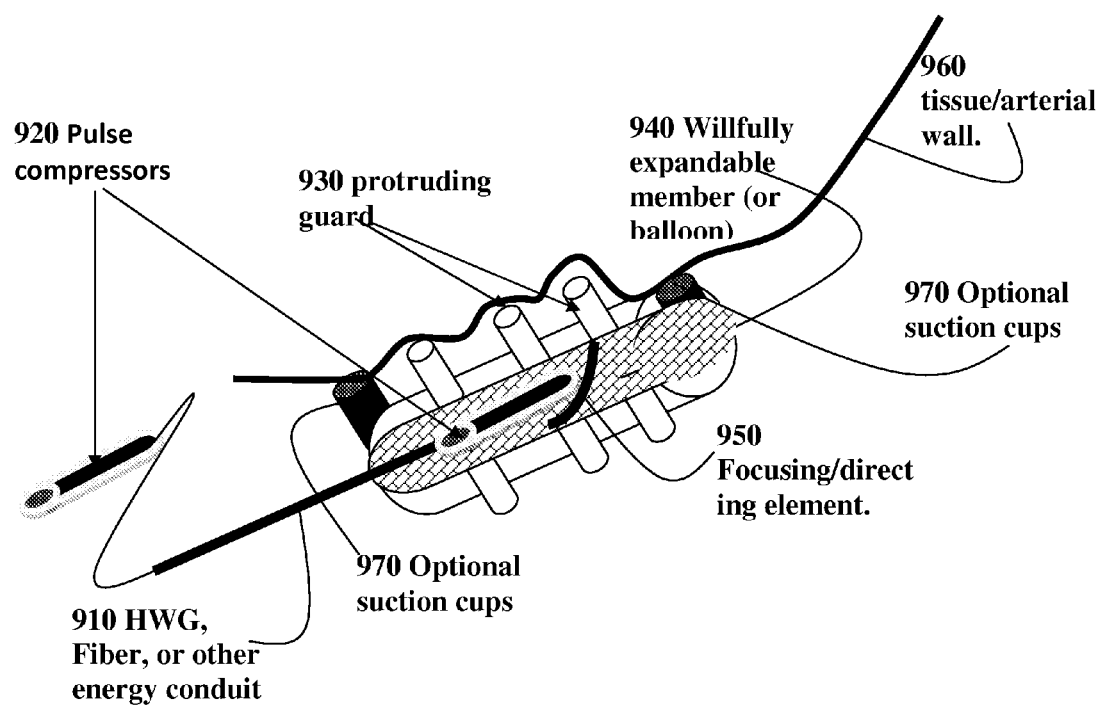
FIG. 9 shows the treatment head and upper sections of a device for treatment of CVD and VP.

A Conduit to Deliver Said Energy from Said Energy Source,

As shown in FIG. 9, the invention further contemplates a device for treating cardiovascular diseases. The device comprises an energy source, the energy source generating an electromagnetic radiation beam; a beam pulsing device, the beam pulsing device pulsing the generated electromagnetic radiation beam at a pulse duration of about 1 femtosecond to about 100 seconds, and at a pulse repetition rate of about 0.1 pulses per second or greater sufficient to allow interaction energy transients caused by the pulsed electromagnetic radiation beam to decay sufficiently such that the material can be modified.

As described in this invention, material modification includes at least one of chemically changing the material, physically changing the material, changing viscoelastic properties of the material, changing optical properties of the material, changing thermal properties of the material, chemically breaking down the material, physically breaking down the material, disintegrating the material, ablating the material, melting the material, and vaporizing the material;

The device further comprise a controller, the controller adjusting characteristics of the electromagnetic radiation beam or the target region such that the generated electromagnetic radiation beam is capable of modifying a desired quantity of the target material, the characteristics including at least one of a diameter of the electromagnetic radiation beam at the target region, a pulse duration, an energy of the electromagnetic radiation beam, a wavelength of the electromagnetic radiation beam, a spatial and/or temporal absorption of the target region, or a spatial and/or temporal scattering of the target region;

The device may comprise further a pulse compressor 920, the pulse compressor spatially and/or temporally compressing the pulses of the pulsed electromagnetic radiation beam as it propagates towards the target material.

As shown in FIG. 9, the device may further comprise a conduit 910 to allow the delivery of said pulse energy to the target material, for example, tissue, or the walls of an artery or blood vessels to be treated 960.

The device conduit 910 may, for example include one or more members selected from the following group:

Hollow Wave Guide (HWG)
Optical fiber
Photonic band gap fiber PBF
A catheter,
Other energy delivering means The pulse of energy from the energy source (not shown in FIG. 9), is coupled to the energy conduit 910. The energy conduit may further comprise one or more pulse duration compressors. The pulse compressors 920 comprise one or more dispersive elements (for example, a prism, a grism, a diffraction grating, a fiber grating, or other components capable of changing the relationship of the pulse frequency components in order to achieve compression of the pulse time duration. The pulse compressor preferably causes the pulse time duration to shrink as it propagates towards the targeted region and the pulse duration, preferably, reaches a minimum at approximately the vicinity of the targeted volume, 980.

The device further comprises an output port allowing the beam 990 or energy pulse to emerge out of the conduit and propagate towards the targeted tissue volume. The device may further comprise a focusing member 920, for example a lens, or optionally a concave mirror, a reflecting and focusing elements, a combination of lenses and mirrors, GRIN Lenses, an optical element, an active optical element, a dynamic focusing element, or other components capable of re-directing or focusing the output energy pulse.

In further embodiment the device's beam redirecting/focusing member 950 and output port 955 may be moved along the axis of the conduit and also be rotate by about 360 degrees rotation about the axis of the conduit.

In yet further embodiment of the present invention, the device may further comprise a plurality of protruding members 930 said protruding members are capable of deforming the targeted tissue surface 960, to allow enhanced penetration of energy into the tissue.

The device may further comprise members 970 capable of exerting suction or apply vacuum or negative pressure to the surface of the targeted tissue, 960. The members capable of applying suction 970 on the tissue surface 960 allow the tissue to be pulled toward the conduit and output port. The suction members 970 may also be able to allow the energy pulse 990 to emerge out of the conduit and enter the tissue 960 at the contact area to which it applies the suction.

Alternatively or additionally, the suction or contact members, 970 may further comprise one or more from a group of
Suction caps,
Vacuum ports,
Pins,
Hooks
Mechanical attachments
Chemical attachments Adhesives Electrical attachments.

In another embodiment the device may further comprise a component capable of undergoing expansion 940 or being pushed outward towards the tissue 960, said expanding member 940 may comprise one or more of a group of A stent, A balloon, A piston, A piston with flexible walls (so that the walls expand as the piston is pushed to compress the enclosed liquid or fluid)

Other member capable expanding or inflating in response to an external signal.

In further embodiment the device may further comprising a plurality of sensor, imaging, feedback, monitoring and control members.

(For example, sensors for heat, pressure, stress, absorption, chemical content, light detection, OCT, microscope, telescope, camera, ultrasound, fluorescence detectors, electrical or electromagnetic detectors, flow meter, ph meter, or other types of sensors, imaging, feedback or monitoring members.

In a further embodiment of the present invention, said monitoring sensors, imaging members, feedback members, or other control and feedback members may further comprise an automated control.

The following discussion follows a summary of the mechanisms responsible for Vulnerable Plaque (VP) creation as described in Wikipedia and includes embodiments provided by the invention that seek to overcome the dangers and problems associated with VP.

Research of vulnerable plaque (VP) has shown it to be an atheromatous plaque which is an unstable collection of white blood cells (primarily macrophages) and lipids (including cholesterol) in the wall of an artery. VP is blamed for causing sudden major problems, such as a heart attack or stroke.

In many cases, a vulnerable plaque has a thin fibrous cap and a large and soft lipid pool underlying the cap. These characteristics together with the usual hemodynamic pulsating expansion during systole and elastic recoil contraction during diastole contribute to a high mechanical stress zone on the fibrous cap of the atheroma, making it prone to rupture.

Increased hemodynamic stress correlates with increased rates of major cardiovascular events associated with exercise, especially exercise beyond levels the individual does routinely. Additionally smoking which restricts blood flow in the capillaries, or unhealthy air quality are also believed to increase the risks of heart attacks.

Generally an atheroma becomes vulnerable if it grows more rapidly and has a thin cover separating it from the bloodstream inside the arterial lumen. Tearing of the cover is called plaque rupture.

Repeated atheroma rupture and healing is one of the mechanisms, perhaps the dominant one, which creates artery stenosis.

Researchers have found that inflammation in the arteries leads to the development of "soft" or vulnerable plaque, which when released aggressively promotes blood clotting.

Researchers now think that vulnerable plaque is formed in the following way:

Lipoprotein particles, which carry fats and cholesterol in the blood stream, are absorbed by the artery wall past the endothelium lining cholesterol is released and then oxidized. This process typically starts in childhood. Oxidized cholesterol is an irritant which causes the release of proteins (called cytokines). The cytokines make the artery wall sticky which leads to accumulation of additional cholesterol. White blood cells (specifically monocytes) squeeze into the artery wall. The white blood cells including those known as macrophages attack and ingest the oxidized cholesterol droplets. The macrophages releasing their fat laden membranes attracts more macrophages. Macrophage-induced-enzymes erode away the fibrous membrane beneath the endothelium in the artery walls and weaken the wall. Mechanical stretching and contraction of the artery, with each heart beat can lead to a rupture in the wall and allows clot-promoting plaque contents to emerge into the blood stream.

Emergence of the contents of the vulnerable plaque into the bloodstream has severe consequences: The sticky cytokines on the artery wall capture blood cells (mainly platelets) that accumulate at the site of injury. When these cells clump together, they form a clot, sometimes large enough to block the artery.

The most frequent cause of a cardiac event following rupture of a vulnerable plaque is blood clotting on top of the site of the ruptured plaque that blocks the lumen of the artery, thereby stopping blood flow to the tissues the artery supplies.

ALSO—Upon rupture, atheroma tissue debris may spill into the blood stream; this debris is often too large (over 5 micrometers) to pass on through the capillaries downstream. In this, the usual situation, the debris obstruct smaller downstream branches of the artery resulting in temporary to permanent end artery/capillary closure with loss of blood supply to, and death of the previously supplied tissues.

The invention presents BOTH 1. a method and a device for a preventive treatment of VP as well as 2. A method and a device for treating blood clots, blood blockage, as well as arteries and the body blood conduits afflicted by blockage, narrowing or obstructions that constrict, reduce, or prevent blood flow.

For a preventive treatment of VP, the invention contemplates a less invasive procedures to be conducted in conjunction with angioplasty, wherein the operator or physician would insert a device as described in the present invention along with a catheter, to disable locations of arterial VP in suspected sites. The device inserted with a catheter through small opening in the patient body, will survey the areterial walls for constrictions or VP locations (for example, using conjugate imaging techniques such as CT, MRI, OCT, Ultrasound, cameras, videos, and Forward Looking Ultrasound among other imaging techniques and devices). When a suspected site is detects, the operator or physician can activate the energy source and direct the treatment to the suspected sites as described herein in the specifications of the present invention. A treatment consists of doses of energy with the characteristics discovered by the inventor that allow said energy doses to penetrate the surface of the arterial walls substantially without damaging or weakening it and modify the VP content underneath the surface. Modification may include vaporization, ablation, coagulation, shrinkage, changes to chemical or physical characteristics, changes to Viscoelstic properties, as well as changes to to mechanical, chemical or thermal properties.

The Sub-surface treatment by the energy reaches the targeted VP underneath the surface of the wall of the arteries by utilizing at least one of the following capabilities of the present invention:

1. Energy spatial focusing below the surface so an above-threshold interaction occurs at the targeted volume under the arteries wall surface.
2. Energy pulse compression wherein the energy pulse duration is shorten with the aid of pulse compressing means to allow the pulse volumetric power density to reach an above-threshold level, and, 3. Modification and/or applying mechanical pressure to the artery wall surface and tissue so that energy penetration into the layers below the surface is enhanced, the VP sites are modified bring about at least some reduction or elimination risks of VP rapture, and to at least partially change the content of the VP so it is less potent in causing blood clotting, substantially without damaging the arteries walls.

Additionally, atheroma rupture may allow bleeding from the lumen into the inner tissue of the atheroma making the atheroma size suddenly increase and protrude into the lumen of the artery producing lumen narrowing or even total obstruction.

While a single ruptured plaque can be identified during autopsy as the cause of a coronary event, there is currently no way to identify a culprit lesion before it ruptures. For this reason, the inventions method of substantially reducing threat of rapture or leakage from VP locations is of very significant importance to reducing the risk of CVD and reducing occurrences of heart attacks or blood clots.

In the present invention we define a lumen (pl. lumina) in biology as the inside space of a tubular structure, such as an artery or intestine Because artery walls typically enlarge in response to enlarging plaques, these plaques do not usually produce much stenosis of the artery lumen. Therefore, they are not detected by cardiac stress tests or angiography, the tests most commonly performed clinically with the goal of predicting susceptibility to future heart attack. Additionally, because these lesions do not produce significant stenoses, they are typically not considered "critical" and/or interventionable by interventional cardiologists, even though research indicates that they are the more important lesions for producing heart attacks.

For this reason the present invention (in one embodiment) proposes utilizing a ablative/diagnostic technique such as LIBS, LIPS, luminescence spectroscopy, or multiphoton spectroscopy (or other type of analysis or imaging known in the art) to detect such VP locations.

In addition, the present invention in another embodiment, proposes using the subsurface-energy-material modification (SSEMM) as described).

The tests most commonly performed clinically with the goal of testing susceptibility to future heart attack include several medical research efforts, starting in the early to mid-1990s, using intravascular ultrasound (IVUS), thermography, near-infrared spectroscopy, careful clinical follow-up and other methods, to predict these lesions and the individuals most prone to future heart attacks. These efforts remain largely research with no useful clinical methods to date (2006).

The present invention also proposes using a "full lumen surface resurfacing" (FLSR) approach—where the material modifying probe or catheter is moved along the lumen and disable VP within the endometrial walls on a "wholesale" basis—i.e. by treating substantially much of surface of the endothelium so that substantially many if not most location of VP within the surface of the arteries are treated as described above so that they substantially pose considerably less risk of erupting or causing heart attack.

Another approach to detecting and understanding plaque behavior, used in research and by a few clinicians, is to use ultrasound to non-invasively measure wall thickness (usually abbreviated IMT) in portions of larger arteries closest to the skin, such as the carotid or femoral arteries. While stability vs. vulnerability cannot be readily distinguished in this way, quantitative baseline measurements of the thickest portions of the arterial wall (locations with the most plaque accumulation). Documenting the IMT, location of each measurement and plaque size, a basis for tracking and partially verifying the effects of medical treatments on the progression, stability or potential regression of plaque, within a given individual over time, may be achieved.

Prevention

Patients can lower their risk for vulnerable plaque rupture in the same ways that they can cut their heart attack risk: take aspirin, eat a proper diet, quit smoking, and begin an exercise program. Researchers also think that obesity and diabetes may be tied to high levels of C-reactive protein.

Treatment

Prior to the presentation of the embodiments of this invention there were no clinically validated detection or treatment methods for vulnerable plaque exist currently.

Current Research

Newer clinical trial results (2007), e.g. the COURAGE trial, have demonstrated that aggressively treating some of the physiologic behavioral factors which promote atheromas with "optimal medical therapy" (not opening stenoses, per-se) produced the most effective results in terms of improving human survival and quality of life for those who have been identified as having already developed advanced cardiovascular disease with many vulnerable plaques.

The following is a useful summary of VP of the online Wikipedia description:

A vulnerable plaque is an atheromatous plaque, an unstable collection of white blood cells (primarily macrophages) and lipids (including cholesterol) in the wall of an artery which is particularly prone to produce sudden major problems, such as a heart attack or stroke.

In many cases, a vulnerable plaque has a thin fibrous cap and a large and soft lipid pool underlying the cap. These characteristics together with the usual hemodynamic pulsating expansion during systole and elastic recoil contraction during diastole contribute to a high mechanical stress zone on the fibrous cap of the atheroma, making it prone to rupture. Increased hemodynamic stress correlates with increased rates of major cardiovascular events associated with exercise, especially exercise beyond levels the individual does routinely.

Generally an atheroma becomes vulnerable if it grows more rapidly and has a thin cover separating it from the bloodstream inside the arterial lumen. Tearing of the cover is called plaque rupture.

Repeated atheroma rupture and healing is one of the mechanisms, perhaps the dominant one, which creates artery stenosis.

Researchers have found that inflammation in the arteries leads to the development of "soft" or vulnerable plaque, which when released aggressively promotes blood clotting.

Researchers now think that vulnerable plaque, (see atherosclerosis) is formed in the following way:

1. Lipoprotein particles, which carry fats and cholesterol in the blood stream, are absorbed by the artery wall, past the endothelium lining; cholesterol is released and then oxidized. This process typically starts in childhood.
2. Oxidized cholesterol is an irritant which causes the release of proteins (called cytokines).
3. The cytokines make the artery wall sticky, which attracts immune-system white blood cells (specifically monocytes).
4. The monocytes squeeze into the artery wall. Once inside, they transform into eating cells called macrophages and ingest the oxidized cholesterol droplets.

5. The macrophages sometimes become so cholesterol and membrane laden that they die in place, releasing their fat laden membranes into the intracellular space. This attracts more macrophages.
6. In some regions of increased macrophage activity, macrophage-induced-enzymes erode away the fibrous membrane beneath the endothelium so that the cover separating the plaque from blood flow in the lumen becomes thin and fragile.
7. Mechanical stretching and contraction of the artery, with each heart beat, results in rupture of the thin covering membrane spewing clot-promoting plaque contents into the blood stream.
8. When this inflammation is combined with other stresses, such as high blood pressure (increased mechanical stretching and contraction of the arteries with each heart beat), it can cause the thin covering over the plaque to split, spilling the contents of the vulnerable plaque into the bloodstream. The sticky cytokines on the artery wall capture blood cells (mainly platelets) that accumulate at the site of injury. When these cells clump together, they form a clot, sometimes large enough to block the artery.
9. The most frequent cause of a cardiac event following rupture of a vulnerable plaque is blood clotting on top of the site of the ruptured plaque that blocks the lumen of the artery, thereby stopping blood flow to the tissues the artery supplies.
10. Upon rupture, atheroma tissue debris may spill into the blood stream; this debris is often too large (over 5 micrometers) to pass on through the capillaries downstream. In this, the usual situation, the debris obstruct smaller downstream branches of the artery resulting in temporary to permanent end artery/capillary closure with loss of blood supply to, and death of the previously supplied tissues. A severe case of this can be seen during angioplasty in the slow clearance of injected contrast down the artery lumen. This situation is often termed non-reflow.
11. Additionally, atheroma rupture may allow bleeding from the lumen into the inner tissue of the atheroma making the atheroma size suddenly increase and protrude into the lumen of the artery producing lumen narrowing or even total obstruction.
12. While a single ruptured plaque can be identified during autopsy as the cause of a coronary event, there is currently no way to identify a culprit lesion before it ruptures.
13. Because artery walls typically enlarge in response to enlarging plaques, these plaques do not usually produce much stenosis of the artery lumen. Therefore, they are not detected by cardiac stress tests or angiography, the tests most commonly performed clinically with the goal of predicting susceptibility to future heart attack. Additionally, because these lesions do not produce significant stenoses, they are typically not considered "critical" and/or interventionable by interventional cardiologists, even though research indicates that they are the more important lesions for producing heart attacks.

The tests most commonly performed clinically with the goal of testing susceptibility to future heart attack include several medical research efforts, starting in the early to mid-1990s, using intravascular ultrasound (IVUS), thermography, near-infrared spectroscopy, careful clinical follow-up and other methods, to predict these lesions and the individuals most prone to future heart attacks. These efforts remain largely research with no useful clinical methods to date.

Another approach to detecting and understanding plaque behavior, used in research and by a few clinicians, is to use ultrasound to non-invasively measure wall thickness (usually abbreviated IMT) in portions of larger arteries closest to the skin, such as the carotid or femoral arteries. While stability vs. vulnerability cannot be readily distinguished in this way, quantitative baseline measurements of the thickest portions of the arterial wall (locations with the most plaque accumulation). Documenting the IMT, location of each measurement and plaque size, a basis for tracking and partially verifying the effects of medical treatments on the progression, stability or potential regression of plaque, within a given individual over time, may be achieved.

Patients can lower their risk for vulnerable plaque rupture in the same ways that they can cut their heart attack risk: take aspirin, eat a proper diet, quit smoking, and begin an exercise program. Researchers also think that obesity and diabetes may be tied to high levels of C-reactive protein.

No clinically validated detection or treatment methods for vulnerable plaque exist currently.

Newer clinical trial results (2007), e.g. the COURAGE trial,[3] have demonstrated that aggressively treating some of the physiologic behavioral factors which promote atheromas with "optimal medical therapy" (not opening stenoses, per se) produced the most effective results in terms of improving human survival and quality of life for those who have been identified as having already developed advanced cardiovascular disease with many vulnerable plaques.

Figure 7:
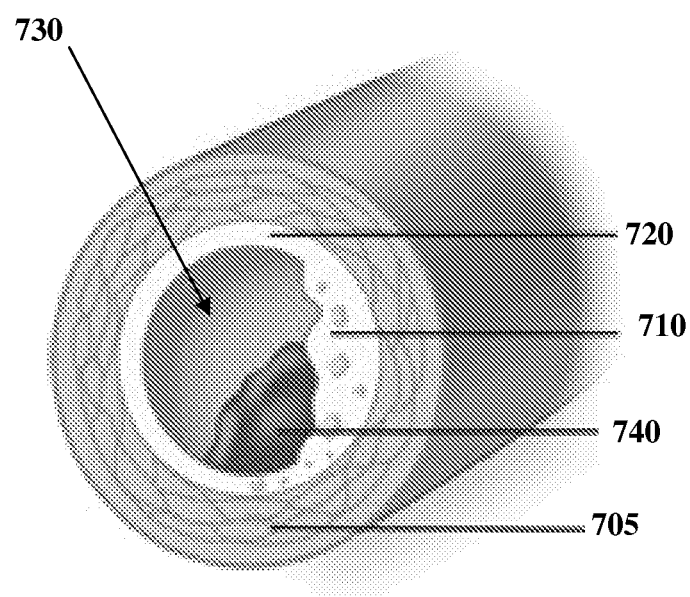
FIG. 7 shows components of an artery along with deposit of plaque and a blood clot.
Figure 8:
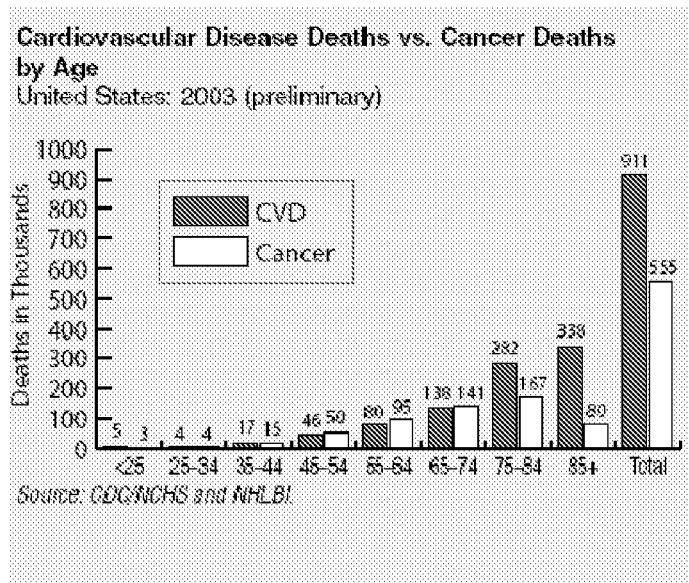
FIG. 8 shows data of CVS death Vs Cancer Death by Age from 2003.

A vulnerable plaque is an atheromatous plaque 710, as seen in FIG. 7, an unstable collection of white blood cells (primarily macrophages) and lipids (including cholesterol) in the wall of an artery which is particularly prone to produce sudden major problems, such as a heart attack or stroke.

In many cases, a vulnerable plaque has a thin fibrous cap and a large and soft lipid pool underlying the cap. These characteristics together with the usual hemodynamic pulsating expansion during systole and elastic recoil contraction during diastole contribute to a high mechanical stress zone on the fibrous cap of the atheroma, making it prone to rupture. Increased hemodynamic stress correlates with increased rates of major cardiovascular events associated with exercise, especially exercise beyond levels the individual does routinely.

Generally an atheroma becomes vulnerable if it grows more rapidly and has a thin cover separating it from the bloodstream inside the arterial lumen 730, as seen in FIG. 7. Tearing of the cover is called plaque rupture.

Repeated atheroma rupture and healing is one of the mechanisms, perhaps the dominant one, which creates artery stenosis.

Inflammation in the arteries leads to the development of "soft" or vulnerable plaque, which when released aggressively promotes blood clotting.

Researchers now think that vulnerable plaque, (see atherosclerosis) is formed in the following way:[1]

Lipoprotein particles, which carry fats and cholesterol in the blood stream, are absorbed by the artery wall 705, past the Endothelium 720 lining.

cholesterol is released and then oxidized. (This process typically starts in childhood).

Oxidized cholesterol is an irritant which causes the release of proteins (called cytokines).

The cytokines make the artery wall sticky and attracts more lipoproteins and white blood cells (specifically monocytes).

The monocytes squeeze into the artery wall and become eating cells called macrophages that ingest the oxidized cholesterol droplets.

The macrophages releasing their fat laden components into the arteries walls or intercellular spaces below the endothelium, a processes that attracts more macrophages. The macrophage below the endothelium also induce enzyme erosion of the fibrous membrane beneath the endothelium. This combined with the mechanical stretching and contraction of the artery, with each heart beat, and can results in rupture of spewing spilling the contents of the vulnerable plaque into the bloodstream and releasing clot-promoting plaque contents into the blood stream. The formation of a blood clot 740, may lead to complete blockage of blood vessels leading to heart attacks or strokes.

Also, the sticky cytokines on the artery wall capture blood cells (mainly platelets) that accumulate at the site of injury. When these cells clump together, they form a clot, sometimes large enough to block the artery.

The most frequent cause of a cardiac event following rupture of a vulnerable plaque is blood clotting on top of the site of the ruptured plaque that blocks the lumen of the artery, thereby stopping blood flow to the tissues the artery supplies.

In addition, another danger is that upon rupture, atheroma tissue debris may spill into the blood stream; this debris is often too large (over 5 micrometers) to pass on through the capillaries downstream. In this, the usual situation, the debris obstruct smaller downstream branches of the artery resulting in temporary to permanent end artery/capillary closure with loss of blood supply to, and death of the previously supplied tissues.

To alleviate this danger during operation, treatment, or diagnostics, the invention proposes using in conjunction with the device or the method proposed herein in the specifications, to utilize a debris collecting member (DCM) wherein said DCM comprises a sieve, a strainer or a filter, 975 to catch and/or collect such life-threatening debris.

Additionally, atheroma rupture may allow bleeding from the lumen into the inner tissue of the atheroma making the atheroma size suddenly increase and protrude into the lumen of the artery producing lumen narrowing or even total obstruction.

In another embodiment the invention contemplates a method for treating cardiovascular diseases by an energy beam, directed towards the a target region of a target material, the interactions between the energy beam and the material providing a modification threshold volumetric power density, the method comprises the following steps:
a) providing a source capable of generating an output beam comprised of a sequence of energy pulses, each energy pulse having a pulse duration in [the] a range of approximately 1 femtosecond to approximately 100 seconds;
b) operating the source and manipulating beam parameters so that a deposited volumetric power density of the beam within a volume of the targeted region is greater than the threshold volumetric power density wherein control of the deposited volumetric power density is achieved by varying at least one of the following parameters: a beam spot size at the target region, a duration of the energy pulses, an energy of the pulses, or a wavelength of the pulsed energy pulses;
c) spatially and temporally varying absorption and/or scattering characteristics of the material at the target region;
d) allowing interaction energy transients caused by the energy pulses to substantially decay so that material modification is effected permitting the controlled, variable rate material modification, the material modification including at least one of the following material modifications: chemical changes of the material, physical changes of the material, changes to viscoelastic properties of the material, changes to optical properties of the material, thermal properties of the material, chemical and physical breakdown of the material, disintegration of the material, ablation of the material, melting of the material, and vaporization of the material;
e) operating the [pulse] source at a pulse repetition rate greater than 0.1 pulses per second until a desired volume of the material in the target region has been modified.

In further elaboration of this embodiment the method further comprises providing a conduit to deliver said pulse energy to the target material.

In further elaboration of this embodiment the method further comprises a conduit that includes one or more members selected from the group of:
Hollow Wave Guide (HWG)
Optical fiber
Photonic band gap fiber PBF
A catheter,
Other energy delivering means In further elaboration of this embodiment the method further comprises the method further comprises coupling the pulsed energy to the conduit and wherein said conduit is further capable of inducing a compression of the pulse duration so that said pulse duration is shortest at the targeted volume.

In further elaboration of this embodiment the method further comprises providing an output member.

In further elaboration of this embodiment the method further comprises the method further comprising the step of providing a focusing member.

In further elaboration of this embodiment the method further comprises providing a focusing member which is chosen from a group that includes:
A lens
A mirror
A concave mirror
A GRIN lens
An optical element
An active optical element
A dynamic focusing element
Other members capable of re-directing or focusing the output pulse.

In further elaboration of this embodiment the method further comprises the method further comprises providing a focusing member that can be moved along the axis of the catheter and/or be stirred or made to spin into 360 degrees.

In further elaboration of this embodiment the method further comprises the method further comprises providing protruding members said protruding members that are capable of contacting and/or pushing the surface of the targeted tissue.

In further elaboration of this embodiment the method further comprises providing a suction and/or attachment members said attachment members are capable of contacting and attaching the target tissue surface to at least one attachment member.

In further elaboration of this embodiment the method further comprises the step of providing attachment members said attachment members are selected among one or more from a group of:
Suction caps
Vacuum ports
Pins
Hooks
Mechanical attachments
Chemical attachments
Adhesives
Electrical attachments In further elaboration of this embodiment the method further comprises the step of providing an expendable member.

In further elaboration of this embodiment the method further comprises the step of providing an expandable member which is one or more selected from a group of
- A stent,
- A balloon,
- A piston,
- Other member capable expanding or inflating in response to an external signal.

In further elaboration of this embodiment the method further comprises the step of providing at least one of the following elements:
- a sensor, an imaging element, a feedback element, means for monitoring and control, camera, microscope, telescope, other means for sensing, imaging, OCT, Ultrasound, fluorescence detector, Spectrally encoded imaging, luminescence emission detector, spectrographs, non-linear imager, or other means for imaging, sensing, feedback and control.

In further elaboration of this embodiment the method further comprises the step of providing an automated control and/or guidance.

Those skilled in the art will appreciate that the foregoing examples and descriptions of various preferred embodiments of the present invention are merely illustrative of the invention as a whole, and that variations in wavelength, pulse duration, pulse repetition rate, as well as beam energy density, may be made within the spirit and scope of the invention. Accordingly, the present invention is not limited to the specific embodiments described herein, but rather is defined by the scope of the appended claims.

What is claimed is:

1. A device for treating CVD comprising:
    an energy source, the energy source generating an electromagnetic radiation beam;
    a beam pulsing device, the beam pulsing device pulsing the generated electromagnetic radiation beam at a pulse repetition rate of about 0.1 pulses per second or greater sufficient to allow interaction energy transients caused by the pulsed electromagnetic radiation beam to decay sufficiently such that a material can be modified,
    wherein the material modification includes at least one of chemically changing the material, physically changing the material, changing viscoelastic properties of the material, changing optical properties of the material, changing thermal properties of the material, chemically breaking down the material, physically breaking down the material, disintegrating the material, ablating the material, melting the material, and vaporizing the material;
    a controller, the controller adjusting characteristics of the electromagnetic radiation beam or a target region such that the generated electromagnetic radiation beam is capable of modifying a desired quantity of a target material, the characteristics including at least one of a diameter of the electromagnetic radiation beam at the target region, a pulse duration, an energy of the electromagnetic radiation beam, a wavelength of the electromagnetic radiation beam, a spatial and/or temporal absorption of the target region, or a spatial and/or temporal scattering of the target region;
    a pulse compressor, the pulse compressor spatially and/or temporally compressing the pulses of the pulsed electromagnetic radiation beam as it propagates towards the target material;
    a conduit to deliver said pulsed electromagnetic radiation beam to the target material, wherein said pulsed electromagnetic radiation beam is coupled to the conduit and wherein said conduit is further capable of inducing a compression of the pulse duration so that said pulse duration is shortest at the targeted volume;
    an output member and a focusing member, wherein the focusing member can be moved along the axis of the catheter and/or be stirred or made to spin into 360 degrees.

2. The device of claim 1, wherein said conduit includes one or more members selected from the group of:
    Hollow Wave Guide (HWG);
    optical fiber;
    photonic band gap fiber PBF;
    a catheter;
    other energy delivering means.

3. The device of claim 1, wherein focusing member is chosen from a group including:
    a lens;
    a mirror;
    a concave mirror;
    a GRIN lens;
    an optical element;
    an active optical element;
    a dynamic focusing element;
    other member capable of re-directing or focusing the output pulse.

4. The device of claim 1, further comprising a plurality of protruding members and said protruding members are capable of pushing the surface of the skin.

5. The device of claim 1, further comprising a suction and/or attachment member said attachment member is capable of attaching the beam pulsing device to the target region.

6. The device of claim 5, wherein said attachment members comprise one or more from a group of:
    suction caps;
    vacuum ports;
    pins;
    hooks;
    mechanical attachments;
    chemical attachments;
    adhesives;
    electrical attachments.

7. The device of claim 5, further comprising expandable member.

8. The device of claim 7, wherein said expandable member is one or more of a group of:
    a stent;
    a balloon;
    a piston;
    other member capable expending or inflating in response to an external signal.

9. The device of claim 7, further comprising sensor, imaging, feedback, monitoring and control members operably coupled to the beam pulsing device.

10. The device of claim 9, further comprising an automated control operably coupled to the sensor, imaging, feedback, monitoring and control members.

11. A method for treating cardiovascular diseases by an energy beam, directed towards a target region of a target material, the interactions between the energy beam and the material providing a modification threshold volumetric power density, the method comprising:
    a) providing a source capable of generating an output beam comprised of a sequence of energy pulses;
    b) operating the source and manipulating beam parameters so that a deposited volumetric power density of the beam within a volume of the targeted region is greater than the threshold volumetric power density wherein control of the deposited volumetric power density is achieved by varying at least one of the following parameters:
a beam spot size at the target region, a duration of the energy pulses, an energy of the pulses, or a wavelength of the pulsed energy pulses;
c) spatially and temporally varying absorption and/or scattering characteristics of the material at the target region;
d) allowing interaction energy transients caused by the energy pulses to substantially decay so that material modification is effected permitting a controlled, variable rate material modification, the material modification including at least one of the following material modifications:
chemical changes of the material, physical changes of the material, changes to viscoelastic properties of the material, changes to optical properties of the material, thermal properties of the material, chemical and physical breakdown of the material, disintegration of the material, ablation of the material, melting of the material, and vaporization of the material;
e) operating the pulse source at a pulse repetition rate greater than 0.1 pulses per second or greater until a desired volume of the material in the target region has been modified;
f) providing a conduit to deliver said pulse energy to the target material, wherein said pulsed energy is coupled to the conduit and wherein said conduit is further capable of inducing a compression of the pulse duration so that said pulse duration is shortest at the targeted volume; and
g) providing a focusing member, wherein said focusing member can be moved along the axis of the catheter and/or be stirred or made to spin into 360 degrees.

12. The method of claim 11, wherein said conduit includes one or more members selected from the group of:
hollow Wave Guide (HWG);
optical fiber;
photonic band gap fiber PBF;
a catheter;
other energy delivering means.

13. The method of claim 11, further comprising an output member.

14. The method of claim 11, wherein said focusing member is chosen from a group including:
a lens;
a mirror;
a concave mirror;
a GRIN lens;
an optical element;
an active optical element;
a dynamic focusing element;
other member capable of re-directing or focusing the output pulse.

15. The method of claim 14, further comprising providing protruding members, said protruding members are capable of pushing the surface of the tissue.

16. The method of claim 14, further comprising providing a suction and/or attachment members, said attachment members are capable of contacting and attaching the target tissue surface to at least one attachment member.

17. The method of claim 16, wherein said attachment members are selected among one or more from a group of:
suction caps;
vacuum ports;
pins;
hooks;
mechanical attachments;
chemical attachments;
adhesives;
electrical attachment.

18. The method of claim 16, further comprising providing an expandable member.

19. The method of claim 18, wherein said expandable member is one or more of a group of:
a stent;
a balloon;
a piston;
other member capable expending or inflating in response to an external signal.

20. The method of claim 19, further comprising providing at least one of the following elements operably coupled to a controller:
a sensor, an imaging element, a feedback element, means for monitoring and control.

21. The method of claim 20, further comprising providing an automated control of generating an output beam.

* * * * *